(12) United States Patent
Kelley et al.

(10) Patent No.: US 9,265,629 B2
(45) Date of Patent: Feb. 23, 2016

(54) FABRIC COVERED POLYMERIC PROSTHETIC LINER

(71) Applicant: The Ohio Willow Wood Company, Mount Sterling, OH (US)

(72) Inventors: Christopher T. Kelley, Grandview Heights, OH (US); James M. Colvin, Hilliard, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 0 days.

(21) Appl. No.: 14/020,165

(22) Filed: Sep. 6, 2013

(65) Prior Publication Data

US 2014/0005800 A1    Jan. 2, 2014

Related U.S. Application Data

(63) Continuation-in-part of application No. 13/078,710, filed on Apr. 1, 2011, now abandoned.

(51) Int. Cl.
*A61F 2/78* (2006.01)

(52) U.S. Cl.
CPC *A61F 2/7812* (2013.01); *A61F 2/78* (2013.01)

(58) Field of Classification Search
CPC .. A61F 2/78; A61F 2/7812; A61F 2002/7818
USPC .......................................................... 623/36
See application file for complete search history.

(56) References Cited

U.S. PATENT DOCUMENTS

| 1,319,637 | A | 10/1919 | Blevens |
| 1,497,219 | A | 6/1924 | Martino |
| 1,748,470 | A | 2/1930 | Domizlaff |
| 2,002,064 | A | 5/1935 | Kohl |
| 2,202,598 | A | 5/1940 | Peterson |

(Continued)

FOREIGN PATENT DOCUMENTS

| CA | 2514390 A1 | 6/2005 |
| CA | 2190764 C | 11/2007 |

(Continued)

OTHER PUBLICATIONS

Kuraray, Thermoplastic Elastomer with High Flexibility and Exquisite Soft Feel, Kuraray new release, Jul. 1, 2010.*

(Continued)

*Primary Examiner* — Bruce E Snow
(74) *Attorney, Agent, or Firm* — Benesch Friedlander Coplan & Aronoff LLP; Benjamen E. Kern (57) ABSTRACT

A prosthetic cushion liner and cushion locking liner for use as a standalone interface between an amputee's residual limb and the interior of a prosthetic socket. The liners include a fabric covering having an open end for introduction of a residual limb and a closed end opposite said open end, and a cushioning block copolymer and plasticizing oil gel composition residing on only an interior surface of the fabric covering. The gel composition includes some amount of a Septon J-Series thermoplastic elastomer material, and/or some amount of a Septon V-Series thermoplastic elastomer material, and/or some amount of a Septon Q-Series thermoplastic elastomer material. The cushion locking liner further includes a distally-located connecting element for coupling the liner to the socket of a prosthesis.

12 Claims, 4 Drawing Sheets

(56) References Cited

U.S. PATENT DOCUMENTS

| | | | |
|---|---|---|---|
| 2,586,045 | A | 2/1952 | Hoza |
| 2,666,208 | A | 1/1954 | Funk |
| 2,671,225 | A | 3/1954 | Schoene et al. |
| 2,703,405 | A | 3/1955 | Smallberg |
| 2,787,266 | A | 4/1957 | Scholl |
| 2,824,559 | A | 2/1958 | Sullivan |
| 3,016,631 | A | 1/1962 | Servin |
| 3,084,685 | A | 4/1963 | Lewis |
| 3,120,711 | A | 2/1964 | Scholl |
| 3,132,648 | A | 5/1964 | Scholl |
| 3,138,156 | A | 6/1964 | Crowell et al. |
| 3,239,478 | A | 3/1966 | Harlan |
| 3,265,765 | A | 8/1966 | Holden et al. |
| 3,375,821 | A | 4/1968 | Meek |
| 3,417,413 | A | 12/1968 | Gage |
| 3,451,232 | A | 6/1969 | Belzidsky |
| 3,457,566 | A | 7/1969 | Artzt |
| 3,520,002 | A | 7/1970 | Wellington |
| 3,548,420 | A | 12/1970 | Spence |
| 3,595,942 | A | 7/1971 | Wald et al. |
| 3,598,127 | A | 8/1971 | Wepsic |
| 3,600,717 | A | 8/1971 | McKeehan |
| 3,613,681 | A | 10/1971 | Adams |
| 3,648,291 | A | 3/1972 | Pankers |
| 3,663,973 | A | 5/1972 | Spence |
| 3,676,387 | A | 7/1972 | Lindlof |
| 3,732,578 | A | 5/1973 | Pollack |
| 3,827,999 | A | 8/1974 | Crossland |
| 3,855,677 | A | 12/1974 | Belzidsky |
| 3,892,239 | A | 7/1975 | Remiro |
| 3,970,081 | A | 7/1976 | Applegate |
| 3,971,194 | A | 7/1976 | Morgan |
| 3,983,870 | A | 10/1976 | Herbert et al. |
| 3,991,424 | A | 11/1976 | Prahl |
| 4,018,646 | A | 4/1977 | Ruffo et al. |
| 4,084,586 | A | 4/1978 | Hettick |
| 4,116,236 | A | 9/1978 | Albert |
| 4,183,984 | A | 1/1980 | Browers et al. |
| 4,194,041 | A | 3/1980 | Gore et al. |
| 4,201,203 | A | 5/1980 | Applegate |
| 4,250,578 | A | 2/1981 | Barlow |
| 4,319,136 | A | 3/1982 | Jinkins |
| 4,369,284 | A | 1/1983 | Chen |
| 4,381,380 | A | 4/1983 | LeVeen et al. |
| 4,474,573 | A | 10/1984 | Detty |
| 4,502,234 | A | 3/1985 | Schaefer et al. |
| 4,517,688 | A | 5/1985 | May et al. |
| 4,542,169 | A | 9/1985 | Costerton |
| 4,590,123 | A | 5/1986 | Hashimoto et al. |
| 4,618,213 | A | 10/1986 | Chen |
| 4,635,626 | A | 1/1987 | Lerman |
| 4,663,413 | A | 5/1987 | Ward et al. |
| 4,671,267 | A | 6/1987 | Stout |
| 4,784,128 | A | 11/1988 | Scheuermann |
| 4,814,375 | A | 3/1989 | Esposito |
| 4,822,371 | A | 4/1989 | Jolly et al. |
| 4,832,010 | A | 5/1989 | Lerman |
| 4,840,635 | A | 6/1989 | Smith et al. |
| 4,842,931 | A | 6/1989 | Zook |
| 4,853,978 | A | 8/1989 | Stockum |
| 4,908,037 | A | 3/1990 | Ross |
| 4,923,474 | A | 5/1990 | Klasson et al. |
| 4,923,475 | A | 5/1990 | Gosthnian et al. |
| 4,928,404 | A | 5/1990 | Scheuermann |
| 4,932,474 | A | 6/1990 | Schroeder et al. |
| 4,961,418 | A | 10/1990 | McLaurin-Smith |
| 4,971,060 | A | 11/1990 | Schneider et al. |
| 4,990,556 | A | 2/1991 | Shimizu et al. |
| 5,007,937 | A | 4/1991 | Fishman et al. |
| 5,016,622 | A | 5/1991 | Norvell |
| 5,038,762 | A | 8/1991 | Hess et al. |
| 5,048,513 | A | 9/1991 | Reinhardt |
| 5,058,573 | A | 10/1991 | Hess et al. |
| 5,083,361 | A | 1/1992 | Rudy |
| 5,098,421 | A | 3/1992 | Zook |
| 5,108,456 | A | 4/1992 | Coonan |
| 5,131,385 | A | 7/1992 | Kuehnegger |
| 5,154,690 | A | 10/1992 | Shiono |
| 5,167,649 | A | 12/1992 | Zook |
| 5,168,577 | A | 12/1992 | Detty |
| 5,181,914 | A | 1/1993 | Zook |
| 5,201,773 | A | 4/1993 | Carideo |
| 5,201,774 | A | 4/1993 | Greene |
| 5,211,667 | A | 5/1993 | Danforth |
| 5,218,056 | A | 6/1993 | Santiyanont et al. |
| 5,221,534 | A | 6/1993 | DesLauriers et al. |
| 5,246,464 | A | 9/1993 | Sabolich |
| 5,258,036 | A | 11/1993 | Edenbaum et al. |
| 5,258,037 | A | 11/1993 | Caspers |
| 5,262,468 | A | 11/1993 | Chen |
| 5,263,923 | A | 11/1993 | Fujimoto |
| 5,263,990 | A | 11/1993 | Handal |
| 5,272,236 | A | 12/1993 | Lai et al. |
| 5,295,483 | A | 3/1994 | Nowacki et al. |
| 5,314,496 | A | 5/1994 | Harris et al. |
| 5,314,497 | A | 5/1994 | Fay et al. |
| 5,334,446 | A | 8/1994 | Quantrille et al. |
| 5,334,646 | A | 8/1994 | Chen |
| 5,336,708 | A | 8/1994 | Chen |
| 5,376,131 | A | 12/1994 | Lenze et al. |
| 5,376,132 | A | 12/1994 | Caspers |
| 5,387,245 | A | 2/1995 | Fay et al. |
| 5,399,627 | A | 3/1995 | Diehl et al. |
| 5,405,405 | A | 4/1995 | Love |
| 5,411,037 | A | 5/1995 | Hess et al. |
| 5,432,703 | A | 7/1995 | Clynch et al. |
| 5,443,525 | A | 8/1995 | Laghi |
| 5,464,384 | A | 11/1995 | Cromartie |
| 5,464,443 | A | 11/1995 | Wilson et al. |
| 5,480,455 | A | 1/1996 | Norvell |
| 5,497,513 | A | 3/1996 | Arabeyre et al. |
| 5,497,789 | A | 3/1996 | Zook |
| 5,507,834 | A | 4/1996 | Laghi |
| 5,507,836 | A | 4/1996 | Pohlig |
| 5,508,334 | A | 4/1996 | Chen |
| 5,534,034 | A | 7/1996 | Caspers |
| 5,538,500 | A | 7/1996 | Peterson |
| 5,555,584 | A | 9/1996 | Moore et al. |
| 5,571,208 | A | 11/1996 | Caspers |
| 5,593,454 | A | 1/1997 | Helmy |
| 5,603,122 | A | 2/1997 | Kania |
| 5,618,882 | A | 4/1997 | Hammond et al. |
| 5,633,286 | A | 5/1997 | Chen |
| 5,656,023 | A | 8/1997 | Caprio et al. |
| 5,728,165 | A | 3/1998 | Brown |
| 5,728,167 | A | 3/1998 | Lohmann |
| 5,728,168 | A | 3/1998 | Laghi |
| 5,746,772 | A | 5/1998 | Jacobs |
| 5,769,809 | A | 6/1998 | Witzel |
| 5,781,652 | A | 7/1998 | Pratt |
| 5,792,531 | A | 8/1998 | Littleton et al. |
| 5,824,111 | A | 10/1998 | Schall et al. |
| 5,830,237 | A | 11/1998 | Kania |
| 5,854,372 | A | 12/1998 | Henze et al. |
| 5,888,216 | A | 3/1999 | Haberman |
| 5,897,517 | A | 4/1999 | Laghi |
| 5,901,060 | A | 5/1999 | Schall et al. |
| 5,904,722 | A | 5/1999 | Caspers |
| 5,911,126 | A | 6/1999 | Massen |
| 5,934,163 | A | 8/1999 | Saunders et al. |
| 5,944,682 | A | 8/1999 | Milana-Panopoulos |
| 5,954,647 | A | 9/1999 | Bova et al. |
| 5,971,194 | A | 10/1999 | Freedland |
| 5,994,612 | A | 11/1999 | Watkins |
| 6,025,067 | A | 2/2000 | Fay |
| 6,059,834 | A | 5/2000 | Springs |
| 6,063,125 | A | 5/2000 | Arbogast et al. |
| 6,075,883 | A | 6/2000 | Stern et al. |
| 6,083,125 | A | 7/2000 | West |
| 6,117,176 | A | 9/2000 | Chen |
| 6,125,197 | A | 9/2000 | Mack et al. |
| 6,136,039 | A | 10/2000 | Kristinsson et al. |
| 6,149,616 | A | 11/2000 | Szlema et al. |
| 6,149,690 | A | 11/2000 | Belzidsky |

(56) References Cited

U.S. PATENT DOCUMENTS

| | | |
|---|---|---|
| 6,177,034 B1 | 1/2001 | Ferrone |
| 6,231,617 B1 | 5/2001 | Fay |
| 6,259,942 B1 | 7/2001 | Westermann et al. |
| 6,358,453 B1 | 3/2002 | Slemker et al. |
| 6,383,148 B1 | 5/2002 | Pusch et al. |
| 6,406,499 B1 | 6/2002 | Kania |
| 6,440,345 B1 | 8/2002 | Hellberg |
| 6,454,812 B1 | 9/2002 | Laghi |
| 6,463,351 B1 | 10/2002 | Clynch |
| 6,485,776 B2 | 11/2002 | Janusson et al. |
| 6,520,964 B2 | 2/2003 | Tallarida et al. |
| 6,552,109 B1 | 4/2003 | Chen |
| 6,592,539 B1 | 7/2003 | Einarsson et al. |
| 6,626,952 B2 | 9/2003 | Janusson et al. |
| 6,665,577 B2 | 12/2003 | Onyshkevych et al. |
| 6,761,742 B2 | 7/2004 | Caspers |
| 6,964,688 B1 | 11/2005 | Kania |
| 6,968,246 B2 | 11/2005 | Watson et al. |
| 7,004,919 B2 | 2/2006 | Gaylord et al. |
| 7,144,429 B2 | 12/2006 | Carstens |
| 7,162,322 B2 | 1/2007 | Arbogast et al. |
| 7,291,182 B1 | 11/2007 | Kania |
| 7,344,568 B2 | 3/2008 | Chen |
| 7,351,264 B2 | 4/2008 | Wilson |
| 7,427,297 B2 | 9/2008 | Patterson et al. |
| 8,308,817 B2 | 11/2012 | Egilsson et al. |
| 2002/0103545 A1 | 8/2002 | Arbogast et al. |
| 2002/0183859 A1 | 12/2002 | Houser |
| 2003/0009354 A1 | 1/2003 | Arbogast et al. |
| 2003/0181989 A1 | 9/2003 | Eberle et al. |
| 2004/0122528 A1 | 6/2004 | Egilsson |
| 2004/0137178 A1 | 7/2004 | Janusson et al. |
| 2004/0243252 A1 | 12/2004 | Carstens |
| 2005/0020951 A1 | 1/2005 | Gaylord et al. |
| 2005/0101693 A1* | 5/2005 | Arbogast et al. ............... 523/122 |
| 2005/0126095 A1 | 6/2005 | Deschamps |
| 2005/0149202 A1 | 7/2005 | Schaffer et al. |
| 2005/0216095 A1 | 9/2005 | Egilsson |
| 2005/0240283 A1 | 10/2005 | Kania |
| 2006/0111792 A1 | 5/2006 | Shannon |
| 2007/0055383 A1 | 3/2007 | King |
| 2007/0080479 A1 | 4/2007 | Arbogast et al. |
| 2007/0150069 A1 | 6/2007 | Takami et al. |
| 2008/0269914 A1 | 10/2008 | Coppens et al. |
| 2009/0076625 A1 | 3/2009 | Groves et al. |
| 2009/0132056 A1 | 5/2009 | Kania |
| 2009/0240344 A1 | 9/2009 | Colvin et al. |
| 2010/0249949 A1 | 9/2010 | Bjarnason et al. |
| 2010/0249950 A1 | 9/2010 | Bielefeld |
| 2010/0274363 A1 | 10/2010 | Laghi et al. |
| 2012/0191218 A1 | 7/2012 | McCarthy |
| 2013/0338793 A1 | 12/2013 | Bernaquer |
| 2014/0058529 A1 | 2/2014 | Schober et al. |

FOREIGN PATENT DOCUMENTS

| | | |
|---|---|---|
| DE | 4321182 C1 | 12/1994 |
| EP | 0086147 A1 | 8/1983 |
| EP | 0362850 A2 | 4/1990 |
| EP | 0374281 A1 | 6/1990 |
| EP | 0762857 B1 | 11/2005 |
| EP | 1618858 A2 | 1/2006 |
| EP | 0955964 B1 | 10/2006 |
| EP | 1736122 A1 | 12/2006 |
| FR | 2581859 A1 | 11/1986 |
| GB | 2188846 A | 10/1987 |
| GB | 2213308 A | 8/1989 |
| GB | 2213380 A | 8/1989 |
| GB | 2261358 A | 5/1993 |
| IS | 8061 A | 10/2005 |
| JP | 64-32861 A | 2/1989 |
| JP | 03160083 A | 7/1991 |
| JP | 03259955 A | 11/1991 |
| JP | 0463887 A | 2/1992 |
| JP | 04261450 A | 9/1992 |
| RU | 1812982 C | 4/1993 |
| SU | 1739990 A1 | 6/1992 |
| WO | 8800032 A1 | 1/1988 |
| WO | 9005401 A1 | 5/1990 |
| WO | 9310732 A1 | 6/1993 |
| WO | 9323472 A1 | 11/1993 |
| WO | 9418263 A1 | 8/1994 |
| WO | 9418638 A1 | 8/1994 |
| WO | 9424965 A1 | 11/1994 |
| WO | 9505792 A1 | 3/1995 |
| WO | 9527756 A | 10/1995 |
| WO | 9527756 A1 | 10/1995 |
| WO | 9531160 A1 | 11/1995 |
| WO | 9629033 A1 | 9/1996 |
| WO | 9804218 A1 | 2/1998 |
| WO | 9830176 A1 | 7/1998 |
| WO | 9925536 A1 | 5/1999 |
| WO | 03003145 A1 | 1/2003 |
| WO | 2005055010 A1 | 6/2005 |
| WO | 2012071048 A1 | 5/2012 |

OTHER PUBLICATIONS

Alpha Cushion and Locking Liner Brochures, Ohio Willow Wood Co., 15441 Scioto Darby Rd., P.O. Box 130, Mt. Sterling, Oh 43143, (800) 848-4930, Jan. 14, 1997.

ALPS Gel-Sheath Fax, ALPS South Corp., 2895 42nd Ave. N., St. Petersburg, FL 33714, (800) 574-5426, Jul. 24, 1997.

Chadderton, H. Clifford, Silopad Soft Socket Gel Liner, Prosthetics, Fall 1995, pp. 49-50.

Cluitmans et al., Experience with respect to ICEROSS system for trans-tibial prosthesis, Prosthetics and Orthotics International, 1994, pp. 78-83.

Comfort Zone Single Socket Gel Liner, Silosheath Product Line, Silipos Advertisement in O&P Business News, p. 16, Jan. 1, 1995.

Comfort Zone, Silosheath Product Line, Silipos Advertisement in O&P Business News, p. 9, Sep. 1, 1994.

Derma Seal Advertisement, Otto Bock Gel-Strumph, unknown place of publication, unknown date.

Elevated Vacuum Responses, Response 6, O&P list serve on oandp. com, Sep. 8, 2008.

Fillauer et al., Evolution and Development of the Silicone Suction Socket (3S) for Below-Knee Prosthesis, Journal Prosthetics and Orthotics, 1989, p. 92, vol. 1, No. 2.

Full Potential Newsletter, Current Trends in Prosthetic-Orthotic Rehabilitation, No. 38, 1995, pp. 1-4.

Gould, Robert; U.S. Appl. No. 08/076,842 filed Jun. 15, 1993, Abandoned Sep. 13, 1995.

Haws, J.R. and Wright, R.F., Block Polymers from Handbook of Thermoplastic Elastomers, edited by Walker, pp. 72-102, published by Van Nostrand Reinhold Co., 1979.

Hole-In-One Prosthetic Sock, Knit-Rite, Inc. Kansas City, MO (Advertisement); Nov. 1995 (2 pages).

IceFlex Endurance Brochure, Distributors in U.S.: Cascade (800) 888-0865, Knit-Rite (800) 821-3094, Orto-Ped (800) 363-8726, PEL (800) 321-1264, SPS (800) 767-7776.

Koch et al., Polyvinylchloride Gel in Orthotics and Prosthetics, Part I, Preparation and Application of Silicone Gel, Orthotics and Prosthetics, Sep. 1971, pp. 16-19.

Koepke et al., Polyvinylchloride Gel in Orthotics and Prosthetics, Part II, Silicone Gel Below-Knee Amputation Prosthesis, Orthocis and Prosthetics, Sep. 1971, pp. 20-22.

Kristinsson, O., The ICECROSS Concept: a discussion of a philosphy, Prosthetics and Orthotics International, pp. 49-55, 1993, vol. 17.

Madigan et al., Technique 3-S Prosthesis: A Preliminary Report, Journal of Pediatric Orthopaedics, 1991, pp. 112-117, vol., No. 1, Raven Press, Ltd., New York.

New Ez Flex Liner. O&P Edge Magazine, Mar. 2009.

New Introductory Price! Double cushion Silosheath, Silosheath Product Line, Silipos Advertisement Unknown Place of Publication, 1994.

(56) References Cited

OTHER PUBLICATIONS

New Introductory Price! Soft Socket Gel-Liner, Silipos advertisement, unknown date and publication.
New Products from Ossur, Icecross, Comfort, The Ultimate in silicon gel suspension from Ossur, the silicon specialist, SPS Orthotic Prosthetic Supplies, (800) 767-7776, Nov. 1997.
O&P Business News, Linking the Orthotic and Prosthetic Profession, Jan. 1, 1995, Silipos Comfort Zone Gel E Roll (Advertisement), Silipos Comfort Zone Single Socket Gel Liner (Advertisement), Soft Socket Gel Liner from Silipos (p. 22), Einstein, Edison & Össur ICEROSS (Advertisement).
Otto Bock OrthoGel-Liner (Unknown Date) (1 page).
PCT Written Opinion for PCT/US97/09036, May 19, 1998.
Silipos Comfort Zone Double/Single Socket Gel Liner (Date Unknown)(4 pages).
Silipos Prosthetics/Orthotics Catalog, Single & Double Socket Gel Liners, p. 9, vol. II, 1997.
SiloLiner Webpage printout, Silipos, Mar. 8, 1999.
Silopad Softsock Package Insert. Filed with Information Disclosure Statement for U.S. Appl. No. 08/076,842 on Sep. 15, 1993.
Silosheath Classic Webpage Printout, Apr. 30, 2001.
Silosheath Soft Socket Gel Liner Brochure, prices good from Mar. 15, 1994 to Jun. 15, 1994, Silipos, 2150 Liberty Drive, L.P.O. Box 211, Niagara Falls, NY 14303 (800) 229-4404.
The Alpha Liner Instruction Booklet, Ohio Willow Wood, Oct. 2, 2002.
Thermoplastic Elastomer with High Flexibility and Exquisite Soft Feel, Kuraray Co. Ltd., Jul. 1, 2010, [retrieved Apr. 27, 2015]. Retrieved from the Internet <URL: http://www.kuraray.co.jp/en/release/2010/100701.html?id=rss>.
Tracer Cad Fabrication, Tracer Central Fabs, 1 web page, http://www.tracercad.com/fabrication.html, Ohio Willow Wood Co., 15441 Scioto Darby Rd., P.O. Box 130, Mt. Sterling, OH 43143, (800) 848-4930, Aug. 15, 2003.
Tracer Cad Products, Omega T. Ring, 1 web page, http://www.tracercad.com/t-ring.html, Ohio Willow Wood Co., 15441 Scioto Darby Rd., P.O. Box 130, Mt. Sterling, OH 43143, (800) 848-4930, Aug. 15, 2003.
Tracer Cad Products, The Tracer Premier System, 1 web page, Ohio Willow Wood Co., 15441 Scioto Darby Rd., P.O. Box 130, Mt. Sterling, OH 43143, (800) 848-4930, Aug. 15, 2003.
Tracercad About Us, The O&P Perspective, 1 web page, http://www.tracercad.com/perspective.html, Ohio Willow Wood Co., 15441 Scioto Darby Rd., P.O. Box 130, Mt. Sterling, OH 43143, (800) 848-4930, Aug. 15, 20013.
Tracercad About Us, Why Omega, 1 web page, http://www/tracercad.com/aboutus.html, Ohio Willow Wood Co., 15441 Scioto Darby Rd., P.O. Box 130, Mt. Sterling, OH 43143, (800) 848-4930, Aug. 15, 2003.
Welcome to Silipos Manual, Handwritten Date 1994.
What is Tracer? 2 web pages, http://www.owwco.com/html, Ohio Willow Wood Co., 15441 Scioto Darby Rd., P.O. Box 130, Mt. Sterling, OH 43143, (800) 848-4930, Aug. 15, 2003.
Zook, Gerald, Soft Viscoelastic Gels: Potentially Valuable Padding and Medicating Materials for Foot Care Products, current Medicine, Oct. 1990, pp. 11-13.
International Search Report and Written Opinion for PCT App. No. PCT/US2014/029993, mailed Aug. 20, 2014.
International Search Report and Written Opinion for PCT App. No. PCT/US2012/033855, mailed Aug. 6, 2012.

\* cited by examiner

FABRIC COVERED POLYMERIC PROSTHETIC LINER

CROSS-REFERENCE TO RELATED APPLICATIONS

This application is a continuation-in-part of prior U.S. patent application Ser. No. 13/078,710 filed on Apr. 1, 2011.

TECHNICAL FIELD

The present invention is directed to a gel and various articles of manufacture using said gel, such as a prosthetic cushion liner and a prosthetic cushion locking liner.

BACKGROUND

Polymeric prosthetic liners (or "liners") have become the interface of choice among amputees due to various beneficial characteristics thereof. These characteristics include, for example, comfort, security of suspension, protection of the residual limb, and ease of use. Modern liner technology allows amputees to employ a liner as the sole (stand-alone) interface between their residual limb (which is also commonly referred to as a residuum or amputation stump) and the interior of a prosthetic socket—in contrast to known wool or knit socks and cushioned socks or sheaths that must be worn in multiple layers and/or various combinations to provide sufficient cushioning and protection to a residual limb.

Prosthetic liners may be non-suspensory in nature. Non-suspensory liners are commonly referred to as "cushion liners." Prosthetic liners may optionally be suspensory in nature and may, therefore, include a docking element that facilitates suspension by mechanical attachment of the liner to the socket of a prosthesis. Suspensory liners are commonly referred to as "locking liners" or "cushion locking liner." Liners can be of standard "off-the-shelf" design, meaning the liner is of generic shape and will fit a range of residual limb shapes and sizes. Alternatively, liners may be custom designed for a particular amputee.

Liners may be comprised of various polymeric materials, including silicone, urethane, and thermoplastic elastomers (TPE) gels. Liners are now commonly made using various block copolymer and mineral oil gel compositions. Such polymeric materials, particularly block copolymer and mineral oil gel compositions, have proven themselves to provide an optimal level of comfort for most users.

It is also known to construct such liners with an outer layer of fabric. For example, the present assignee produces patented fabric-covered liners having an interior of exposed polymeric gel for contacting and cushioning an amputee's residual limb, and an integrated outer layer of fabric for, among other things, increasing the wear resistance of the liner, and facilitating donning/doffing and insertion of the liner-covered residual limb into a prosthetic socket.

As would be understood by one of skill in the art, liners as described above are frequently used by lower limb amputees. Lower limb amputees generally fall into one of two categories: above knee (AK) amputees and below knee (BK) amputees. In the case of a BK amputee, the knee joint is still present and, thus, a bending of the residual limb at the knee joint will still occur during ambulation. While the prosthetic hard socket of a BK prosthesis is generally recessed to accommodate the knee joint, BK amputees typically wear a liner that extends over the knee joint to some point along the thigh of the residual limb. Consequently, bending of the knee joint occurs under cover of the liner.

In a typical below-knee (BK) prosthesis an amputee's stump tends to "piston" in the socket: during ambulation the stump will come up in the socket of the prosthesis until the attaching means holding the prosthesis to the wearer causes the prosthesis to lift with the stump. On the way down, air may be trapped between the residuum and stump sock, or between the prosthesis socket and sock, or between a socket liner and a sock.

With wool and cotton socks which tend to breathe and which are not airtight, this pistoning effect is not a major problem with regard to the generation of sound effects. Since wool and cotton tend not to tightly form fit a residuum, the amputee typically packs a material around the residuum once it is placed into the prosthetic device or adds additional socks to increase thickness or puts on thicker socks in order to provide necessary fit. However, for socks which do not breathe and which are made from, e.g., polymeric material, a problem occurs when the residuum pistons in the prosthetic device: sound effects such as sucking and gurgling noises are generated which are obtrusive and inappropriate, often embarrassing the wearer. In addition, such air pockets produce non-uniform pressures and loading discontinuities on the skin, irritating it.

Finally, many amputees experience a swelling of the stump. When the residuum is in a prosthetic socket the stump tends to contract significantly, and when taken out of the socket the stump tends to expand within minutes of removal. This expansion and contraction of the residuum contributes to the development of air pockets and the generation of obtrusive noises since a sock which may have provided a comfortable fit on the expanded stump becomes a loose fit with air pocket opportunities when the residuum is placed inside the prosthetic socket. In addition, and over time, an amputee's residuum tends to adjust in size, usually shrinking. As these changes occur they increase the tendency for the pistoning effect, described above, to occur. In addition to the embarrassment caused by the sound effects generated by pistoning, cushioned socks which allow or promote air pocket formation quickly wear out and, if not replaced often, lead to lesions, etc. on the residuum.

Known cushioned residuum sheaths and socks are frequently purely tubular in shape, but may also be conical in shape. In either case, these devices often do not provide a form fit on an amputee's residuum. Further, regardless of whether such sheaths/socks are provided with internal and/or external cushioning material they frequently fail to avoid air pockets. While a stump may generally have a roughly conical or cubical shape there are invariably recessed areas on, e.g., the medial side of the prominent tibia bone. Generally, on the left side of a below knee residual limb, the recessed area will be predominantly on the right side of the tibia bone. There is also typically a smaller recessed area on the left side. For right side residual limbs the predominant recessed area is on the left side of the bone, with smaller recessed areas on the right side. Usually the greatest recess occurs immediately below the patella, on either side. In addition, left side amputees typically have a right side bias to the bony prominence of the below knee stump, and right side amputees have a similar bias to the left side. Conventional tubular or conical elastic socks simply cannot account for these several variable conditions without using extremely high levels of elastic tension which compress the outer-most points along the stump's circumference, causing discomfort and a non-uniform fit.

Amputees typically attach a prosthetic limb to their residual limb by means of a rigid socket, liner, and a suspension means. The rigid socket is often custom fabricated to match the shape of the intended users residual limb and may be made of thermoplastic or fiber-reinforced thermoset materials, but can also be made from wood, metal, etc. Since such hard materials are generally uncomfortable when in intimate contact with the skin over long periods of time, especially under load bearing conditions, liners and/or prosthetic socks are often used as interface members between the hard socket and the residual limb to increase comfort. Early liners were commonly made of an open cell foam, such as Pelite or Kemblo, but were also made of silicone, urethane, etc., type of materials. See, for example, U.S. Pat. No. 5,258,037 and U.S. Pat. No. 5,376,132, both incorporated herein by reference. Prosthetic socks, as mentioned above, may be made of wool, cotton, synthetic materials, etc., and amputees tend to prefer liners and socks which are easily changed to facilitate cleaning, to accommodate volume changes in the residual limb, or to accommodate different user activities.

Suspension systems which help to hold a prosthetic limb in place may or may not be an integral part of the rigid socket and/or liner. Examples of suspension systems include supracondylar or waist belt, joint and corset systems, neoprene or latex sleeves, socket ears which grip the condyles, suction or pin and lock systems such as those where the pin is attached to a liner and the lock is attached to a hard socket, etc. Examples of various suspension systems may be found in U.S. Pat. No. 4,923,474, U.S. Pat. No. 4,923,475, U.S. Pat. No. 5,007,937, U.S. Pat. No. 5,108,456, U.S. Pat. No. 5,201,773, U.S. Pat. No. 5,201,774, U.S. Pat. No. 5,246,464, U.S. Pat. No. 5,263,923, U.S. Pat. No. 5,314,497, U.S. Pat. No. 5,387,245, U.S. Pat. No. 5,376,131 and U.S. Pat. No. 5,405,405, all incorporated herein by reference.

As block copolymer based prosthetic liners have become increasingly popular, it can be understood that further development of prosthetic liners using such materials would be desirable. The present invention is directed to such a further development.

SUMMARY

A prosthetic cushion liner and cushion locking liner of the present invention is designed to enclose at least the portion of a residual limb that will be located in a prosthetic socket. As such, a liner of the present invention generally includes an open end for allowing introduction of the residual limb, and a closed end opposite the open end. The closed end generally abuts and cushions the distal end of the residual limb when the liner is worn. Such a liner may be used by an upper or lower extremity amputee.

A liner of the present invention is comprised of a polymeric material with a fabric outer covering. As such materials have proven to be especially effective at cushioning and protecting residual limbs while simultaneously providing amputees with a high level of comfort, the polymeric material used in a liner of the present invention is a block copolymer and plasticizing (e.g., mineral) oil gel composition, which may include additional ingredients such as, without limitation, Vitamin E. More particularly, the block copolymer and mineral oil gel compositions used in a liner of the present invention include some amount of one or a combination of Septon™ J-Series thermoplastic elastomer, Septon™ V-series thermoplastic elastomer, and/or Septon™ Q-Series thermoplastic elastomer.

The J-Series thermoplastic elastomer mentioned above incorporates hydrogenated styrenic thermoplastic elastomers and extremely low-hardness gel material to produce a compound that is particularly well-suited for use in a block copolymer and mineral oil gel-based prosthetic liner of the present invention. The V-Series thermoplastic elastomer mentioned above is also a hydrogenated styrenic elastomer, but contains cross-linkable hard blocks that render the material reactive and makes it possible to produce compounds with higher than normal heat and oil resistance. The Q-series thermoplastic elastomer is particularly well-suited to the design of polymer alloys.

Once constructed, a prosthetic liner of the present invention includes a polymeric material interior and a fabric exterior. When used with a prosthesis, the polymeric material of the liner interior is in contact with the skin of a residual limb and the fabric exterior is in contact with the interior of a prosthetic socket.

Because the polymeric material of the liner interior will be in contact with the skin of a residual limb when the liner is worn, the polymeric material is preferably smooth and continuous in nature such that there are no seams or other discontinuities that may cause amputee discomfort. A liner of the present invention will typically protect and cushion the entire portion of a residual limb residing in a prosthetic socket.

While a liner of the present invention may be of the cushion liner variety, other embodiments are constructed as cushion locking liners. To this end, a liner of the present invention may include a connecting element (adapter) at the closed (distal) end for facilitating coupling of the liner to the socket of a prosthetic limb. Such connecting elements may be designed with a special accordion shape that provides for increased comfort when the liner is worn by better conforming to the distal shape of the residual limb.

A better understanding of a prosthetic liner of the present invention can be gained by review of the following description of several exemplary embodiments thereof, along with the associated accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 3:
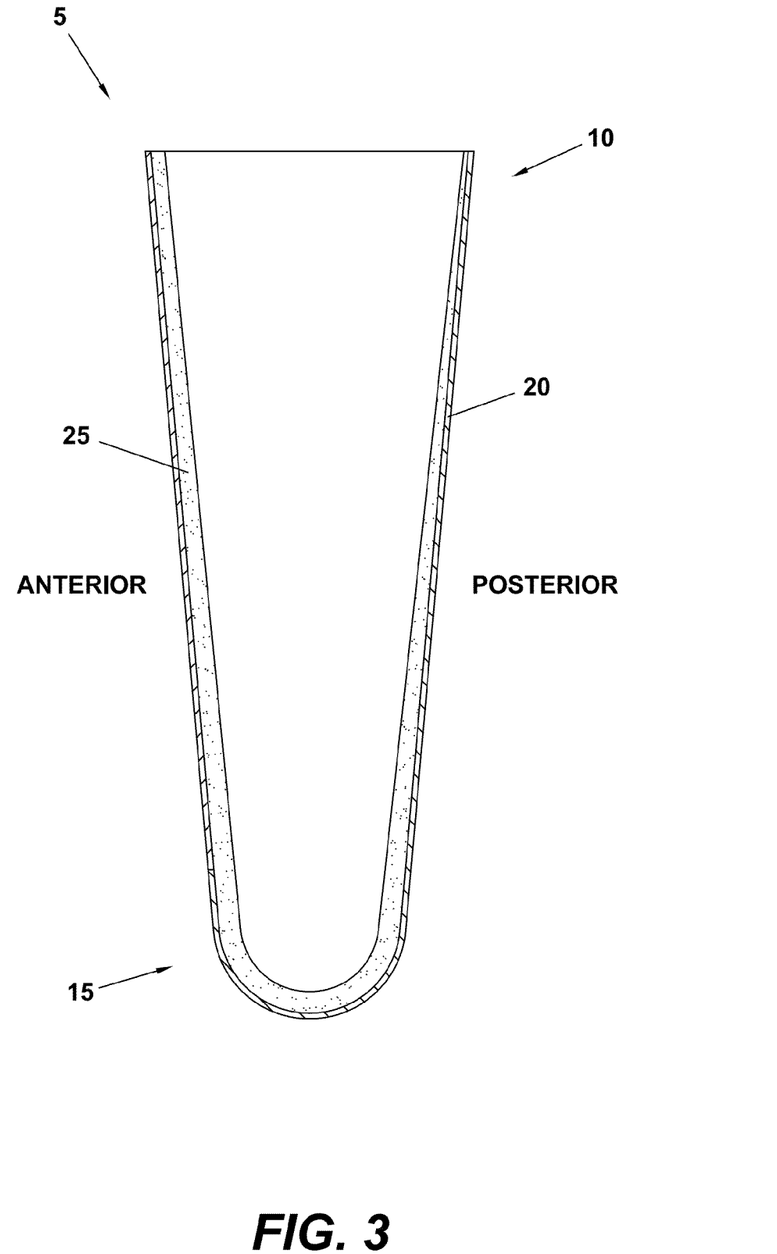
FIG. 3 is a cross-sectional view of an exemplary prosthetic liner of the present invention having an asymmetric polymeric material distribution.
Figure 4A:
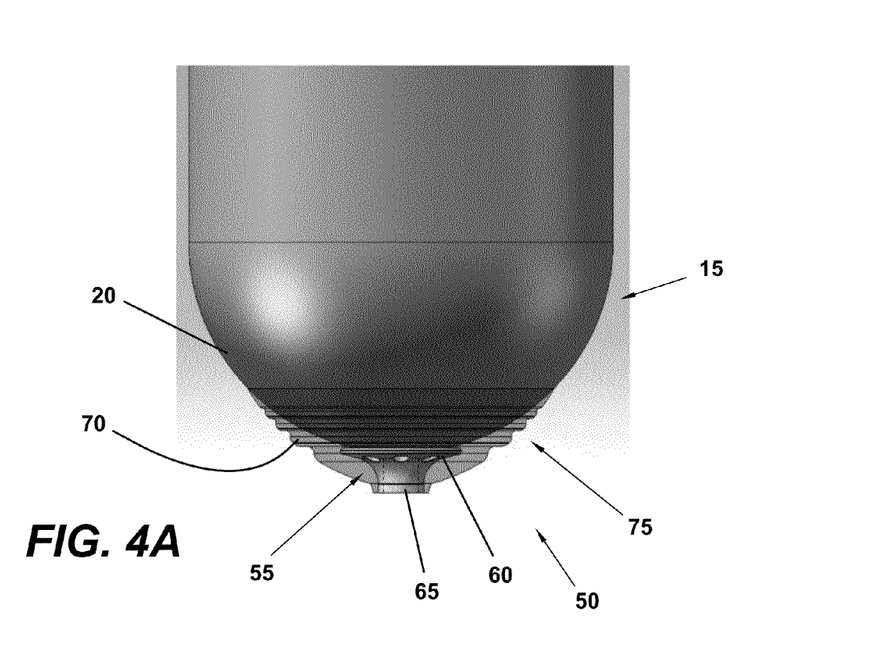
FIG. 4A is a detailed view in partial transparency of an exemplary docking element located at the closed end of a liner of the present invention.
Figure 4B:
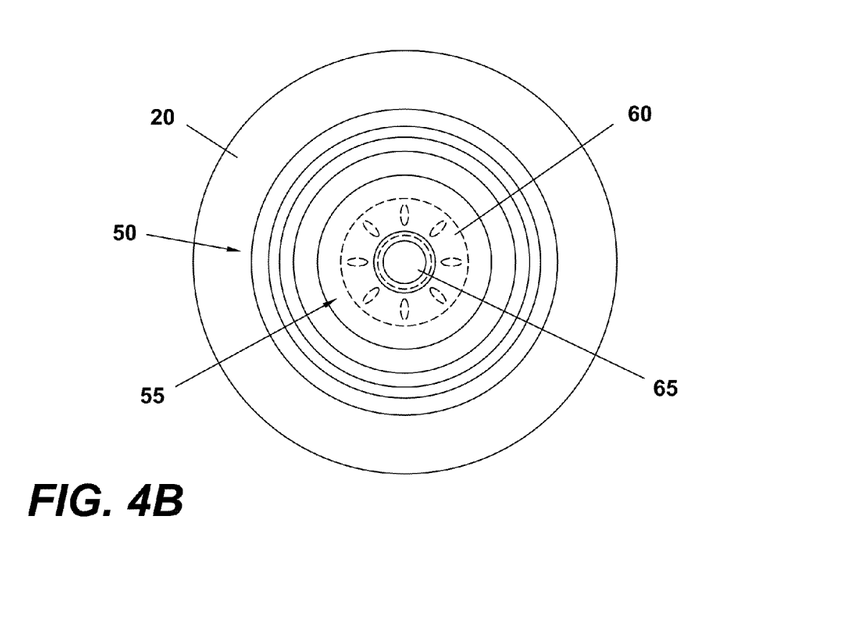
FIG. 4B is a bottom view of the docking element of FIG. 4A.

A first embodiment of a below knee (BK) prosthetic cushion liner 5 of the present invention is depicted in FIGS. 1A-1B and FIGS. 2-3. An exemplary embodiment of a cushion locking liner of the present invention is illustrated in FIGS. 4A-4B, which cushion locking liner may have the same or a similar fabric-gel construction as that shown in FIGS. 1A-1B and FIGS. 2-3. The cushion liner and cushion locking liner of the present invention may be hereinafter referred to simply as a "liner." While the liner shown in the drawing figures is a BK liner, liners of the present invention may also be above knee (AK) liners for use by trans-femoral amputees.

Figure 1A:
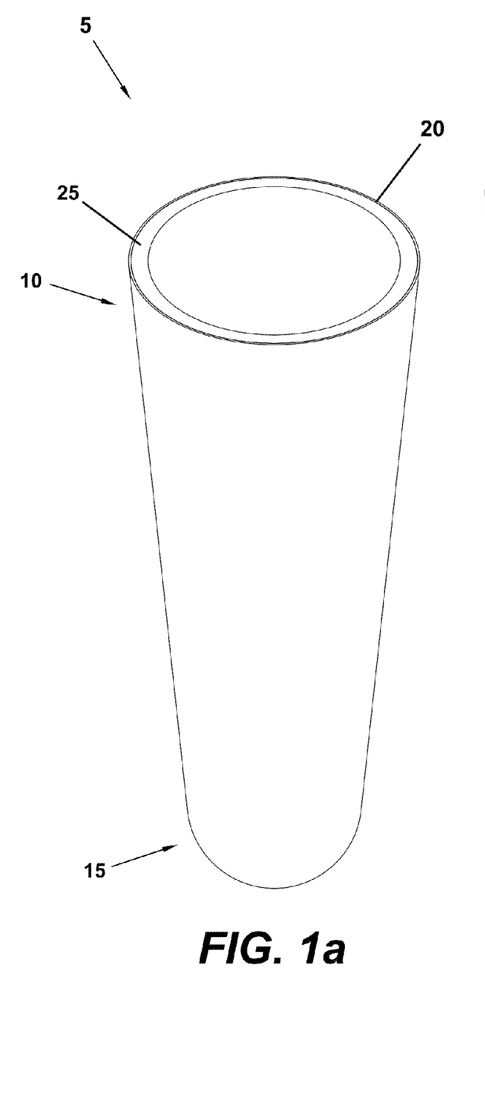
FIGS. 1A and 1B show an exemplary embodiment of a prosthetic liner of the present invention.
Figure 1B:
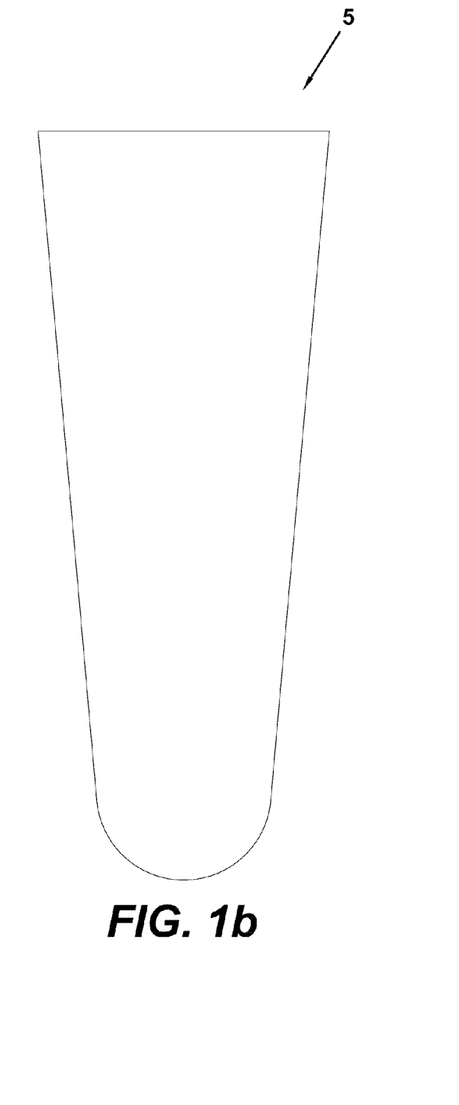
Figure 2:
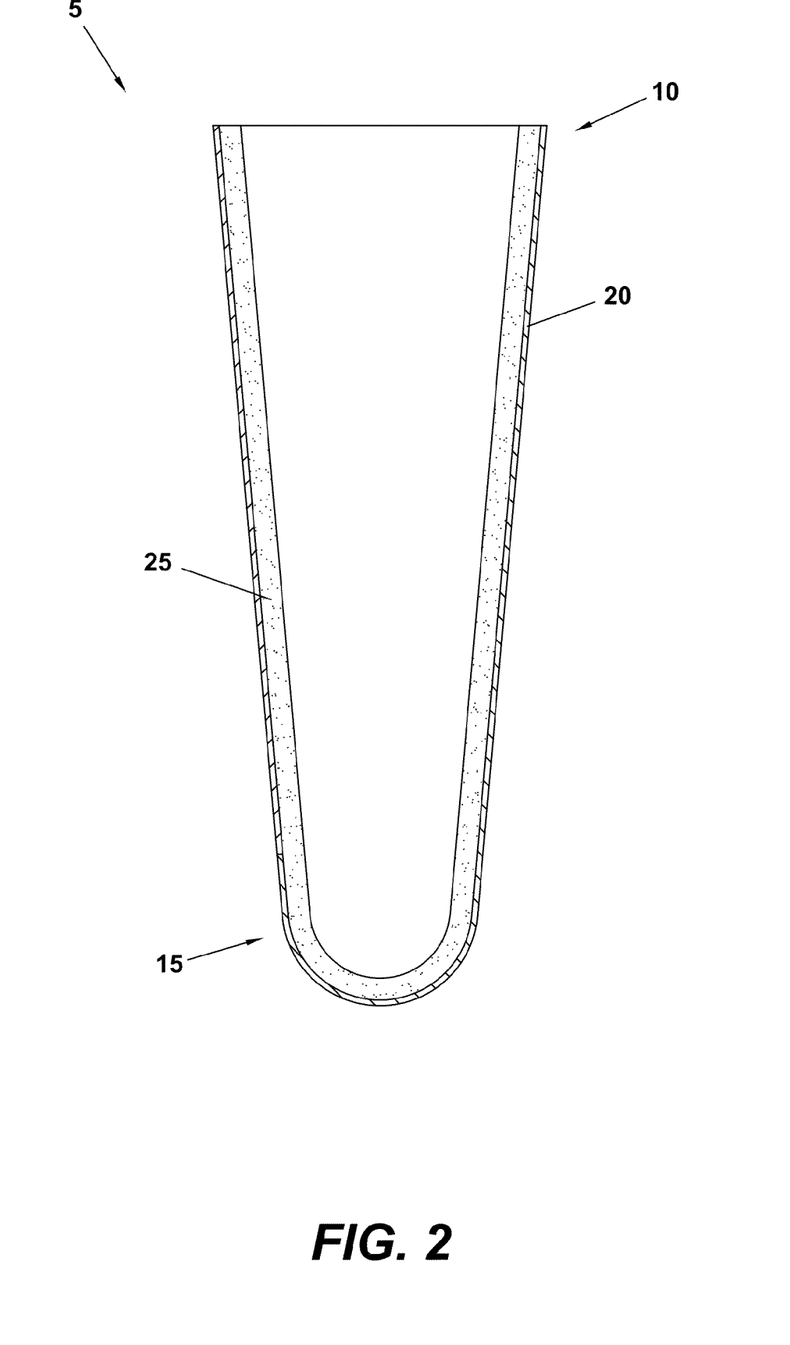
FIG. 2 is a cross-sectional view of an exemplary prosthetic liner of the present invention having a symmetric polymeric material distribution.

As shown, the liner 5 includes an open end 10 for permitting insertion of a residual limb, and a closed end 15 opposite the open end 10. The interior of the liner 5 is comprised of a polymeric material 25, while the exterior of the liner 5 is comprised of fabric 20. The polymeric material 25 will be in contact with the skin of the residual limb when the liner 5 is worn. The fabric 20 is arranged to be in contact with the interior of a prosthetic socket when the liner 5 is used with a prosthetic limb.

Because the polymeric material of the liner interior will be in contact with the skin of a residual limb when the liner is worn, the polymeric material is generally smooth and continuous in nature such there are no seams or other discontinuities that may cause amputee discomfort. Typically, the polymeric material will extend completely to the edge of the fabric at the open end of the liner, such that the entire interior surface of the fabric is covered therewith. Alternatively, it is also possible that some length of fabric may remain devoid of polymeric material so as to form a band or cuff of fabric at the open end of the liner. It is preferred, however, that the polymeric material extend along the fabric to a length that is at least equivalent to the depth of a prosthetic socket cavity with which the liner will be used. Consequently, a liner of the present invention will protect and cushion the entire portion of a residual limb residing in a prosthetic socket.

The fabric portion 20 of a liner of the present invention may be comprised of various fabrics, preferably fabrics that are resistant to the bleed-through of the underlying polymeric material 25. Preferably, but not necessarily, the fabric portion 20 of a liner of the present invention is comprised of a stretch-controlling fabric that is used to control the overall longitudinal elasticity of the liner 5. An explanation of such fabrics and the construction of a liner using such fabrics is described in U.S. patent application Ser. No. 12/711,234, filed May 4, 2010, which application is hereby incorporated by reference in its entirety. Other useable fabrics may include various stretchable non-woven materials and fiber-on-end fabrics such as Wearforce® composites from Xymid, LLC.

The polymeric material 25 used in all embodiments of a liner of the present invention is a block copolymer and plasticizing oil gel composition. For example, one preferable plasticizing oil is mineral oil, more preferably a purified mineral oil and, even more preferably, USP grade mineral oil. The gel composition may include other ingredients such as, without limitation, antioxidants, skin conditioning agents, astringents, biocides, medicaments, etc.

The block copolymer gel compositions used to produce embodiments of a liner of the present invention may include some amount of a Septon™ J-Series thermoplastic elastomer material and/or some amount of a Septon™ V-Series thermoplastic elastomer material, and/or some amount of a Septon™ Q-Series thermoplastic elastomer, all of which are available from Kuraray America, Inc. in Houston, Tex. Block copolymer gel compositions used to produce a liner of the invention may also include some amount of an additional (different) thermoplastic elastomer(s) such as, without limitation, another Septon thermoplastic elastomer. The additional thermoplastic elastomer may function, at least in part, as a detackifying agent.

The Septon J-Series material incorporates hydrogenated styrenic thermoplastic elastomers and extremely low-hardness gel material to produce a composition that is particularly well-suited for use in a block copolymer and mineral oil gel-based prosthetic liner of the present invention. According to the Kuraray website as of the date of this filing, advantageous properties of the J-Series thermoplastic elastomers include: high plasticity; high strength and superior mechanical performance including compression set and tear resistance; high molten liquidity, which is excellent for polymer processing; superior shock-absorption and vibration dampening performance; soft feel; excellent low-temperature properties; and low density/weight savings vs. many other materials. Further exemplary J-Series compound characteristics are provided in the following tables.

| SEPTON J Series Representative Compound Properties | | | | |
|---|---|---|---|---|
| | Unit | Using SEPTON J Series | Using Existing SEPTON Product | Remarks |
| Hardness | | | | |
| (Type A) | | 0 | 0 | Flexibility, soft feel |
| (Shore OO) | | 14 | 28 | |
| Impact resilience rate | % | 36 | 71 | Shock absorbing/ vibration dampening properties |
| Melt flow rate | | | | |
| 160 deg. C., 21N | g/10 min | 34 | 3 | Low melt viscosity |
| 200 deg. C., 21N | g/10 min | >400 | 76 | High processability |
| Compression set | | | | |
| 40 deg. C. | % | 9 | 10 | Mechanical performance on par with existing products |
| 70 deg. C. | % | 59 | 51 | |

(From Kuraray research)

| SEPTON ™ J-Series Representative Compound Properties | | | | | |
|---|---|---|---|---|---|
| | | Compound 1 (Approximate hardness 0 <Type A>) | | Compound 2 (Approximate hardness 15 <Type A>) | |
| | | Using SEPTON ™ J Series | Using existing SEPTON ™ product | Using SEPTON ™ J Series | Using existing SEPTON ™ product |
| Hardness | Type A | 0 | 0 | 14 | 15 |
| | Type C | 8 | 15 | 43 | 45 |

SEPTON™ J-Series Representative Compound Properties

|  |  | Compound 1 (Approximate hardness 0 <Type A>) | | Compound 2 (Approximate hardness 15 <Type A>) | |
| --- | --- | --- | --- | --- | --- |
|  |  | Using SEPTON™ J Series | Using existing SEPTON™ product | Using SEPTON™ J Series | Using existing SEPTON™ product |
| Compression set |  |  |  |  |  |
| 40° C. | (%) | 9 | 10 | 11 | 15 |
| 70° C. | (%) | 59 | 51 | 8 | 27 |
| Impact resilience rate | (%) | 36 | 71 | 36 | 57 |
| Melt flow rate |  |  |  |  |  |
| 160° C., 21N | (g/10 min) | 34 | 3 | no data | no data |
| 160° C., 21N | (g/10 min) | no data | 6 | 3 | 1 |

(Tested by KURARAY CO., LTD.)

The Septon V-Series material also incorporates hydrogenated styrenic thermoplastic elastomers, but with a reactive/cross-linkable hard block and soft block. The V-series material is characterized as exhibiting excellent heat resistance and durability, while simultaneously possessing good elasticity and the ability to produce a low hardness compound (e.g., Shore 30A). The V-series material is also characterized as providing good miscibility with polyolefins and styrenic resins and to have a low specific gravity and good low temperature properties. Further exemplary V-Series elastomer properties and associated exemplary compound characteristics are provided in the following tables.

Typical Properties of SEPTON V-Series

| Grade Type |  | V9461 | V9475 | V9827 | Measurement Method |
| --- | --- | --- | --- | --- | --- |
| Hard Constituent Content | wt % | 30 | 30 | 30 |  |
| Specific Gravity |  | 0.89 | 0.89 | 0.90 | ISO 1183 |
| Hardness (Shore A) |  | — | — | 78 | ISO7619 |
| Tensile Properties |  |  |  |  |  |
| 100% Modulus | MPa | — | — | 2.5 | ISO 37 |
| Tensile Strength | MPa | — | — | 24 |  |
| Elongation | % | — | — | 560 |  |
| Melt Flow Rate |  |  |  |  |  |
| 230° C., 21N | g/10 min | No Flow | No Flow | 3.5 | ISO 1133 |
| 230° C., 21N | g/10 min | No Flow | No Flow | 6 |  |
| Solution Viscosity |  |  |  |  |  |
| 5 wt % | mPa · s | 90 | 240 | — | Toluene Solution 30° C. |
| 10 wt % | mPa · s | — | — | 23 |  |
| Physical Form |  | Powder | Powder | Pellet |  |

(Tested by KURARAY CO., LTD.)

SEPTON™ V-Series Representative Compound Properties

|  |  | 1 | 2 | 3 | Measurement Method |
| --- | --- | --- | --- | --- | --- |
| SEPTON™ V9461 | Parts by mass | 100 | 100 | 100 |  |
| Process Oil |  | 200 | 100 | 100 |  |
| Polypropylene (homo MI = 1) |  | 25 | 27.3 | 50 |  |
| Organic Peroxide |  | 4.6 | 3.5 | 4.6 |  |
| Crosslink co-agent |  | 8 | 6 | 8 |  |
| Anti-Oxidant |  | 0.3 | 0.3 | 0.3 |  |
| Hardness (Shore A) |  | 37 | 61 | 78 | ISO7619 |
| Tensile Properties |  |  |  |  |  |
| 100% Modulus | MPa | 0.7 | 1.7 | 3.1 | ISO 37 |
| Tensile Strength | MPa | 2.9 | 6.7 | 8.4 |  |
| Elongation | % | 420 | 470 | 400 |  |
| Compression Set (70° C., 22 hrs) | % | 19 | 26 | 33 | ISO 7743 |
| Compression Set (120° C., 22 hrs) | % | 21 | 26 | 37 |  |
| Melt Flow Rate (210° C., 98N) | g/10 min | 11 | 7 | 27 | ISO 1133 |

(Tested by KURARAY CO., LTD.)

The Septon Q-Series material also incorporates thermoplastic elastomers, and is particularly well-suited to the design of polymer alloys. The Q-series material is characterized as exhibiting excellent abrasion and scratch resistance, while being very lightweight and having excellent adhesion over olefinic materials. The Q-series material is also characterized as exhibiting superior hydrolysis resistance.

A block copolymer and plasticizing oil gel composition of the invention includes some amount of one or a combination of J-Series, V-Series and/or Q-Series materials, in conjunction with a number of other materials that may be provided for compounding, tackifying or other material property altering purposes. Such materials may include, without limitation, mineral and or other plasticizing oils, polyethylene (PE), antioxidants, other skin conditioning agents, astringents, biocides, medicaments, etc.

The general composition of two exemplary and non-limiting examples of block copolymer and plasticizing oil gel materials according to the invention are shown in the table below. Other non-listed materials may also be present in various amounts.

Exemplary Gel Compositions (by approximate weight %)

| MATERIAL | MINERAL OIL | J-SERIES | V-SERIES | PE |
|---|---|---|---|---|
| 1 | 75%-85% | 15%-20% | 0%-5% | 0.1%-0.5% |
| 2 | 75%-85% | 0%-5% | 15%-25% | 0%-0.5% |

* Total thermoplastic elastomer weight % is preferably 15%-25%.

A block copolymer and plasticizing oil gel composition that includes J-Series, V-Series and/or Q-Series material may have varying degrees of hardness. It has been found, however, that a gel composition having a hardness of between about 15-35 on the Shore 00 scale should provide optimal comfort for most users. Various amounts of PE may be added to adjust the hardness in some embodiments. The thickness of the polymeric layer of a liner of the present invention is preferably between about 0.150-0.50 inches, but may be thicker in some cases.

At least three standard geometries may be provided for both the exemplary cushion liners and the exemplary cushion locking liners. These geometries may be a uniform wall (as exemplified in FIG. 2), a tapered wall (as exemplified in FIG. 3), and a contoured wall (not shown). A recessed configuration in which a localized thinning of the gel in the area of the liner that will overlie the back of the knee or the elbow crease is also possible in all liner embodiments.

The uniform wall cushion and cushion locking liner simply comprise a uniform thickness of gel. Tapered wall cushion liner and cushion locking liners are generally those having a layer of gel which is thicker distally for additional padding (and because most shrinkage of the residual limb occurs at this point of the limb) and thinner proximally (near the open end of the liner) to blend in and interface more easily with the residual limb. The taper may be uniform along both the anterior or posterior sides of the liner, or may be more pronounced along the posterior side (as shown in FIG. 3). Contoured wall cushion liners and cushion locking liners have an uneven distribution of gel throughout to provide cushion effects where needed and, in exemplary embodiments, have a thinner posterior middle and upper to allow maximum range of motion optionally with a thicker distal end both anterior— medial and anterior—later with less thickness in the region between these two areas so as to pad typical bony prominences. Contoured wall liners are often thicker distally and custom shapes can easily be provided to satisfy the individual user.

Liners of the present invention may also be of multi-layer polymeric construction. Such a construction is described in U.S. patent application Ser. No. 12/407,362, filed Mar. 19, 2009 and 61/037,765, filed Mar. 19, 2008, both of which are incorporated by reference herein.

Cushion locking liners of the present invention include a connecting (attachment) element for coupling the distal end of the liner to the socket of a prosthesis. The connecting element may be of various design, as evidenced by the line of locking liners previously and currently available from the application assignee, The Ohio Willow Wood Company.

One particular exemplary embodiment of a connecting element 50 of the present invention is illustrated in FIGS. 4A-4B. This connecting element 50 includes a metallic threaded T-nut 55 that is attached to the fabric 20 of the liner at the closed end 15 thereof by an overlying and substantially encasing semi-flexible umbrella 70.

As shown, the T-nut 55 portion of the connecting element 50 includes a base portion 60 from which extends a hollow, internally-threaded boss 65. Preferably, at least the interior surface of the base portion 60 of the T-nut 55 is concave so as to better conform to the rounded distal shape of the liner once a residual limb is inserted therein. The threaded boss 65 is provided to receive and retain a like-threaded pin, lanyard connector or other connecting element (not shown) that can be used to attach the liner to a mating coupling component associated with a socket of a prosthesis. Such connecting elements are well know to those of skill in the art.

The encasing umbrella portion 70 of the connecting element 50 may be comprised of polyurethane, which bonds to the fabric at the closed end of the liner and secures the T-nut 55 in position thereon. It may also be possible to substitute a hard silicone rubber or another similar material for the umbrella 70. The design of this umbrella 70 differs from known designs in that this umbrella is preferably provided with an accordion configuration. That is, as best shown in FIGS. 4A-4B, the umbrella 70 has a stepped configuration 75 that allows for a slight collapse or compression of the umbrella as the weight of an amputee presses the closed end of an associated liner into the bottom of the prosthetic socket. By allowing for a slight collapse or compression of the umbrella 70, the connecting element 50 is able to better conform to the shape of a residual limb, thereby providing increased comfort for amputees. Other locking liners may use an umbrella of other than the depicted accordion configuration, such as an umbrella of smooth configuration.

Liners of the present invention may be donned by inversion and rolling such that the polymeric material does not drag against the skin. In this manner, the cushioning polymeric material encloses the limb and/or device without sliding or friction. The fabric exterior slides against itself, preventing the sticking together of the polymeric material. Therefore, no lubricant, talcum powder, etc. is required during donning. A liner of the present invention may be doffed (removed) by simply unrolling it from the residual limb.

If desired, the polymeric material may include antioxidants such as Vitamins A, B and C or any other antioxidants commonly used in polymers and which can weep out on a time release basis. In addition, skin conditioning agents may be added to the polymeric material to soothe the skin during wear. Such skin conditioners may include mineral oil, baby oil, etc., which may be added to the polymeric material prior to its application to the fabric. Astringents, biocides, medicaments, etc., may be added or applied to the polymeric material to prohibit infection, heal sores on the residuum, etc.

Manufacturing of a liner of the present invention obviously involves application of the polymeric material to the fabric. This process may occur by dipping, spraying, brushing, rolling, etc. Preferably, but not necessarily, liners of the present invention are manufactured by compression molding using a female die cavity, and a male mold core over which the fabric is placed before insertion of the core into the cavity. It may be possible to similarly produce a liner of the present invention by injection molding.

While certain embodiments of the present invention are described in detail above, the scope of the invention is not to be considered limited by such disclosure, and modifications are possible without departing from the spirit of the invention as evidenced by the following claims.

What is claimed is:

1. A prosthetic cushion liner, comprising:
  a fabric covering having an open end for introduction of a residual limb and a closed end opposite the open end; and
  a continuous layer of a gel composition residing on an interior surface of the fabric covering, the gel composition comprising:

(1) a plasticizing oil;
(2) a first thermoplastic elastomer, the first thermoplastic elastomer comprising a hydrogenated styrenic thermoplastic elastomer; and
(3) polyethylene, in an amount of between about 0.1 weight percent and about 0.5 weight percent, wherein the gel composition has a Shore 00 hardness of between about 15 and about 35.

2. The prosthetic cushion liner of claim 1, wherein the gel composition further comprises a second thermoplastic elastomer, the second thermoplastic elastomer comprising a styrenic thermoplastic elastomer comprising crosslinkable hard blocks.

3. The prosthetic cushion liner of claim 1, wherein the plasticizing oil is present in the gel composition in an amount of between about 75 weight percent and about 85 weight percent.

4. The prosthetic cushion liner of claim 1, wherein the first thermoplastic elastomer is present in the gel composition in an amount of between about 15 weight percent and about 20 weight percent.

5. The prosthetic cushion liner of claim 1, wherein the gel composition further comprises a detackifying agent.

6. The prosthetic cushion liner of claim 1, wherein the plasticizing oil comprises a mineral oil.

7. A prosthetic cushion locking liner, comprising:
a fabric covering having an open end for introduction of a residual limb and a closed end opposite the open end;
a continuous layer of a gel composition residing on an interior surface of the fabric covering, the gel composition comprising:
(1) a plasticizing oil;
(2) a first thermoplastic elastomer comprising a hydrogenated styrenic thermoplastic elastomer; and
(3) polyethylene, in an amount of between about 0.1 weight percent and about 0.5 weight percent, wherein the gel composition has a Shore 00 hardness of between about 15 and about 35; and
a docking element attached to the fabric covering at the closed end for coupling the prosthetic cushion locking liner to a socket portion of a prosthetic limb.

8. The prosthetic cushion locking liner of claim 7, wherein the gel composition further comprises a second thermoplastic elastomer, the second thermoplastic elastomer comprising a styrenic thermoplastic elastomer comprising crosslinkable hard blocks.

9. The prosthetic cushion locking liner of claim 7, wherein the plasticizing oil is present in the gel composition in an amount of between about 75 weight percent and about 85 weight percent.

10. The prosthetic cushion locking liner of claim 7, wherein the first thermoplastic elastomer is present in the gel composition in an amount of between about 15 weight percent and about 20 weight percent.

11. The prosthetic cushion locking liner of claim 7, wherein the gel composition further comprises a detackifying agent.

12. The prosthetic cushion locking liner of claim 7, wherein the plasticizing oil comprises a mineral oil.

* * * * *